US005820872A

United States Patent [19]
Edelson et al.

[11] Patent Number: 5,820,872
[45] Date of Patent: Oct. 13, 1998

[54] METHODS AND COMPOSITIONS FOR IMPROVING THE EFFECTIVENESS OF X-IRRADIATION THERAPY FOR THE TREATMENT OF AN INTERNAL SOLID TUMOR

[75] Inventors: Richard L. Edelson, Westport; Francis P. Gasparro, Hamden, both of Conn.

[73] Assignee: Yale University, New Haven, Conn.

[21] Appl. No.: 100,691

[22] Filed: Jul. 30, 1993

Related U.S. Application Data

[63] Continuation-in-part of Ser. No. 977,672, Nov. 18, 1992, Pat. No. 5,651,993.
[51] Int. Cl.$^6$ .......................... A61K 35/14; A61K 41/00; A61K 45/05
[52] U.S. Cl. .................... 424/277.1; 424/93.71; 424/534; 424/577; 435/2; 514/908; 604/4; 604/6; 604/20; 604/27; 604/28
[58] Field of Search ................................ 424/93 V, 577, 424/88, 89, 92, 277.1, 93.71, 534; 435/2; 514/908; 604/4, 6, 20, 27, 28

[56] References Cited

U.S. PATENT DOCUMENTS

| | | |
|---|---|---|
| 4,670,386 | 6/1987 | Sugaar . |
| 4,753,884 | 6/1988 | Kit et al. . |
| 4,838,852 | 6/1989 | Edelson . |
| 4,895,717 | 1/1990 | Witter . |
| 5,147,289 | 9/1992 | Edelson . |

OTHER PUBLICATIONS

The Cancer Journal 2(11):378–82, Oct. 1989.
BLUT 60(4): 215–218, Apr. 1990.
"Dictionary Of Immunology", W.J. Herbert et al. (ed.), published by Blackwell Scientific Publications (Oxford), see p. 33, 1985.
"Introduction to Veterinary Immunolgy", I. Tizard (ed.), published by W.B. Saunders Company (Phil), see p. 20, 1982.
Carbone et al. J. Exp. Med. 167:1767–1779 1988.
Freeman et al. Radiation and Oncology 24:155–162 1992.
Kuten et al. Strahlenther Onkol 167:392–396 1991.
Kaye et al. N. Eng. J. of Medicine 321(6):1784–1789 1989.
Carbone et al. J. Exp Med 169: 603–612 Mar. 1989.
Lanzavecchia A. Science 260: 937–944 May 14, 1993.
Paul, W.E. Fundamental Immunology 3rd Ed. Raven Press NY 1993 1222–1223.
Cohen Science 262: 841–843 Nov. 1993.
Roitt, I., Essential Immunology, 7th Ed., Blackwell Scientific Publications, Oxford, England, 1991, pp. 120–127.
Tsomides, T. et al., Naturally Processed Viral Peptides Recognized by Cytotoxic T Lymphocytes on Cells Chronically Infected by Human Immunodeficiency Virus Type 1, J. Exp. Med. 180:1283–1293 (1994).
Kannagi, M. et al., Expression of the Target Antigen for Cytotoxic T Lymphocytes on Adult T–cell Leukemia Cells, Int. J. Cancer 54:582–588 (1993).

Riott, I.M., "Essential Immunology", Blackwell Scientific Publications, London, England, pp. 26–31, 140–151 (1991).
Cundari, E. et al., "Non–Specific Incision of DNA Due to the Presence of 8–Methoxypsoralen Photoinduced Interstrand Cross–Links in *Saccharomyces cerevisiae*", Mutation Research, 264:97–102 (1991).
Averbeck, D. et al., "Mutagenic and Recombinogenic Action of DNA Monadducts Photoinduced by the Bifunctional Furocoumarin 8–Methoxypsoralen in Yeast (*Saccharomyces cerevisiae*)", Photochemistry and Photobiology, 45(3):371–379 (1987).
Ullrich, S.E., "Systemic Immunosuppression of Cell–Mediated Immune Reactions by a Monofunctional Psoralen plus Ultraviolet A Radiation", Photodermatology, Photoimmunology and Photomedicine, 8:116–122 (1991).
Alcalay, J. et al., "Local Suppression of Contact Hypersensitivity in Mice by a Monofunctional Psoralen Plus UVA Radiation", Photochemistry and Photobiology, 50(2):217–220 (1989).
Edelson, R., et al., "Treatment of Cutaneous T–Cell Lymphoma By Extracorporeal Photochemotherapy", N. Engl. J. Med. 316:297–303 (1987).
Edelson, R., "Light–Activated Drugs", Scientific American 256(8): 68–75 (1988).
Edelson, R., "Photopheresis: A Clinically Relevant Immunobiologic Response Modifier", Annals of N.Y. Academy of Sciences 636: 154–164 (1991).
Edelson, R., et al., "Photopheresis Update", Prog. Dermatol. 25(3): 1–6 (1991).
Rook, A., et al., Arch. Dermatol. 127:1535–1540 (1991), "Combined Therapy for Sezary Syndrome With Extracorporeal Photochemotherapy and Low–Dose Interferon Alfa Therapy".
Heald, P.W., et al., Yale J. Biol. Med. 62:629–638 (1989), "Photopheresis Therapy of Cutaneous T–Cell Lymphoma: The Yale—New Haven Hospital Experience".
Edelson, R., Yale J. Biol. Med. 62:565–577 (1989), "Photopheresis: A New Therapeutic Concept".
Rook, A.H., et al., Ciba Foundation Symposium 146, New York, John Wiley & Sons, (1989) 171–177, "Extracorporeal photochemotherapy in the treatment of cutaneous T cell lymphoma and autoimmune disorders affecting the skin".

(List continued on next page.)

*Primary Examiner*—Anthony C. Caputa
*Attorney, Agent, or Firm*—Wolf, Greenfield & Sacks, P.C.

[57] ABSTRACT

Methods and pharmaceutical compositions for improving the effectiveness of radiation therapy for treating a subject having an internal solid tumor malignancy are disclosed. The methods include irradiating the tumor to release tumor-derived antigens in vivo, preparing a cellular vaccine including the isolated antigens admixed with a preparation of altered antigen presenting cells and administering the cellular vaccine to the subject. In the preferred embodiments, the antigen presenting cells are leukocytes that have been photochemically altered by subjecting the cells to photopheresis.

26 Claims, 2 Drawing Sheets

OTHER PUBLICATIONS

Rook, A., "Photopheresis in the Treatment of Autoimmune Disease: Experience with *Pemphigus Vulgaris* and Systemic Sclerosis", Annals of N.Y. Academy of Science 636:209–216 (1991).

Malawista, S. et al., "Photopheresis for Rheumatoid Arthritis", Annals of N.Y. Academy of Science 636:217–226 (1991).

F. Latron, "A Critical Role for Conserved Residues in the Cleft of HLA–A2 in the Presentation of a Nonapeptide to T–cells", Science 257:964–967 (1992).

Gasparro, F., et al., "The Excitation of 8–methoxypsoralens with Visible Light: Reversed Phase HPLC Quantitation of Monoadducts and Crosslinks", Photochemistry and Photobiology 57:1007–1010.

Rock et al., "Reassociation with $Beta_2$–microglobulin is necessary for $K_b$ class I major histocompatibility complex binding of exogenous peptides", Proc. Natl. Acad. Sci. (USA) 87: 7517–7521 (1990).

Malane, M. and Gasparro, F., "T Cell Molecular Targets for Psoralens", Annals of N.Y. Academy of Science 636:196–208 (1991).

Berger et al., "The Medical and Biological Effects of Light", Annals of N.Y. Academy of Science 453:80–90 (1985).

Calzavara–Pinton, et al., "A Reappraisal of the Use of 5–Methoxy–psoralen in the Therapy of Psoriasis", exptl. Dermatol. 1:46–51 (1992).

Yang et al., "8–Methoxypsoralen–DNA Adducts in Patients Treated with 8–Methoxypsoralen and Ultraviolet A Light", J. Invest. Dermatol. 92:59–63 (1989).

Ljunggren et al., "Empty MHC Class I Molecules Come Out In The Cold", Nature 346:476–480 (1990).

Heald, P.W., "Correspondence", 28(6)1023–1024 (1993).

Edelson, R.L., "Photopheresis: Present and Future Aspects", J. J. Photochem. Photobiol. B. Biol, 10:165–174 (1990).

Holloway, K.B. et al., "Therapeutic Alternatives in Cutaneous T–Cell Lymphoma", J. Amer. Acad. Dermtol. 27(3):367–378 (1992).

Robinet, E. et al. "Evidence for Tumor Necrosis Factor–alpha Involvement in the Optimal Induction of Class I Allospecific Cytotoxic T Cells", J. Immunol. 144:4555–4561 (1990).

Vowels, B.R. et al. "Extracorporeal Photochemotherapy Induces the Production of Tumor Necrosis factor–alpha by Monocytes: Implications for the Treatment of Cutaneous T–Cell Lymphoma and Systemic Sclerosis", J. Invest. Dermatol. 98:686–692 (1992).

Grunfeld, C. and Palladino, M.A., Jr., "Tumor Necrosis Factor: Immunologic, Antitumor, Metabolic, and Cardiovascular Activities", Adv. Intern. Med. 35:45–72 (1990).

Heald P. et al., Chapter 78, "Cutaneous T–Cell Lymphomas", In Hematology: Basic Principles and Practice, Churchill Livinstone Press, New York, NY 1991.

Heald, P. et al., Hematology 2nd Ed., Basic Principles of Practice, Churchill Livinstone Press, N.Y., "Cutaneous T–Cell Lymphomas" (unpublished, in press).

METHODS AND COMPOSITIONS FOR IMPROVING THE EFFECTIVENESS OF X-IRRADIATION THERAPY FOR THE TREATMENT OF AN INTERNAL SOLID TUMOR

RELATED APPLICATIONS

This application is a continuation in part of U.S. application Ser. No. 07/977,672, filed Nov. 18, 1992, now issued as U.S. Pat. No. 5,651,993, the entire contents of which are incorporated herein by reference.

GOVERNMENT SUPPORT

This invention was made with government support under Contract No. 2R01CA43058-09A1 awarded by the National Institutes of Health. The government has certain rights in the invention.

FIELD OF THE INVENTION

This invention relates to an improved method of cancer therapy. More particularly, the invention relates to methods and pharmaceutical compositions for improving the effectiveness of radiation therapy for treating a subject having an internal solid tumor malignancy by combining irradiation therapy with photopheresis.

BACKGROUND OF THE INVENTION

Cutaneous T cell lymphoma (CTCL) is a malignancy of the immune system that is caused by a massive expansion of a single clone of aberrant T cells. The choice of treatment for CTCL depends upon the extent of the disease state, as well as the general health and age of the patient. In general, early stage disease limited to the skin is treated with sequential topical therapies such as topical nitrogen mustard, psoralen phototherapy ("PUVA", i.e., administration of oral psoralen followed by UVA irradiation of the skin) and total-skin electron beam therapy (TSEB). Later stage disease, e.g., Sezary syndrome, is treated with extracorporeal photochemotherapy ("photopheresis").

Photopheresis for the treatment of cutaneous T cell lymphoma was introduced by Edelson in 1987 (Edelson, R., et al., N. Engl. J. Med. 316:297–303 (1987)). Although relatively new, photopheresis is now considered standard therapy for the erythrodermic variants of CTCL (Edelson, R., "Light-activated Drugs", Scientific American 256(8): 68–75 (1988); Edelson, R., "Photopheresis: A Clinically Relevant Immunobiologic Response Modifier", Annals of N.Y. Academy of Sciences 636:154–164 (1991). The therapy includes two steps: (1) irradiating a preparation of the patient's leukocytes in the presence of a photoactivatable agent (e.g., 8-methoxypsoralen, "8-MOP") to photochemically alter the cells and (2) reinfusing the photochemically altered cells.

Not all CTCL patients with erythroderma respond to photopheresis therapy. Those CTCL patients who do respond have a median survival time of more than 62 months, i.e., approximately twice as long as patients treated with other modalities (Edelson, R., et al., Prog. Dermatol. 25(3):1–6 (1991)). However, because up to 25% of patients with CTCL have a limited response to photopheresis, adjunctive TSEB therapy, chemotherapy (e.g., oral methotrexate (Rook, A., et al., Arch. Dermatol. 127:1535–1540 (1991)) or subcutaneous interferon alfa-2b (Heald, P. W., et al., Yale J. Biol. Med. 62:629–638 (1989) has recently been introduced.

The mechanism of action of photopheresis has not completely been elucidated. Exposure of a malignant T cell clone to 8-MOP and ultraviolet light, followed by return of the irradiated, damaged cells to the patient, appears to elicit a specific response to the aberrant T cells, which response is mediated by T cell surface receptors. Consistent with this hypothesis is the production of a heightened immunity against the pathogenic clone(s) of T cells following reinfusion of irradiated blood leukocytes (Edelson R., et al., N. Engl. J. Med. 316:297–303 (1987); Edelson, R., Yale J. Biol. Med. 62:565–577 (1989); Rook, A. H., et al., Ciba Foundation Symposium 146, New York, John Wiley & Sons, (1989) 171–177).

T cell receptors mediate a cellular immune response by recognizing a particular antigen only when the antigen is associated with a surface marker on an antigen presenting cell. The surface markers belong to a group of molecules known as the major histocompatibility complex (MHC). Binding of the T cell receptor to the antigen/MHC molecule on the antigen presenting cell induces changes in the T cell. These changes collectively comprise a cell-mediated immune response.

Two signals are primarily responsible for inducing the T cell mediated response to an antigen that is associated with an antigen presenting cell. A first signal is generated following binding of the T cell to the antigen on the antigen presenting cell. A second, co-stimulatory signal is sent by "accessory" membrane molecules or soluble messengers from the antigen presenting cell to the responding T cell. These soluble intercellular messengers regulate the amplitude and duration of the immune response and are given the generic term, cytokines. Cytokines include the group previously referred to in the literature as lymphokines, monokines, interleukins, interferons and tumor necrosis factor (Essential Immunology, seventh edition, Blackwell Scientific Publications, Oxford, Great Britain, 1991, pp. 140–150). If the antigen presenting cell does not send the second signal, the T cell is effectively paralyzed, i.e., unable to mount an immune response to the antigen. Certain types of antigen presenting cells, e.g., resting T cells, are unable to send the second signal. Accordingly, in the absence of exogenous cytokine or other second signal, such resting T cells which also function as antigen presenting cells down-regulate an immune response to the presented antigen and lead to antigen specific immunologic paralysis of the T cell whose membrane receptor has been engaged. Other types of antigen presenting cells, e.g., monocytes, are able to release cytokines. Accordingly, monocytes which have been stimulated to release cytokines up-regulate an immune response to the presented antigen.

In addition to CTCL and scleroderma, photopheresis has been used for the treatment of several other autoimmune disorders, including pemphigus vulgaris, systemic sclerosis (Rook, A., "Photopheresis in the Treatment of Autoimmune Disease: Experience with Pemphigus Vulgaris and Systemic Sclerosis", Annals of N.Y. Academy of Science 636:209–216 (1991) and rheumatoid arthritis (Malawista, S., et al., "Photopheresis for Rheumatoid Arthritis", Annals of N.Y. Academy of Science 636:217–226 (1991). Other preliminary trials currently in progress which show promising results for photopheresis therapy include autoimmune or type I insulin-dependent diabetes, cardiac transplant rejection, AIDS-related complex and acute graft-vs.-host disease.

In summary, photopheresis has been demonstrated to produce a generalized clinical benefit for a variety of autoimmune diseases that are characterized by a disorder in T cell regulation. Absent from the list of disease states reported in the prior art to be amenable to photopheresis therapy are diseases for which clonal expansion of circulating, aberrant T-cells has not been implicated including, for example, solid tumor malignancies associated with cancers that are difficult to treat, e.g., cancers of the lung, breast, ovaries, uterus, prostrate, testicles, liver, pancreas, stomach, squamous cell carcinoma of the oral phalynx, fibrosarcomas, kidney, bladder, brain, spinal cord, malignant melonoma and metastatic squamous cell carcinoma of the skin. To date, treatment of such solid tumor malignancies is limited to surgery, irradiation, and/or chemotherapy (see e.g., Harrison's Principles of Internal Medicine, 12th ed., eds. J. D. Wilson et al., McGraw-Hill, Inc., N.Y., N.Y. (1991)).

Although the use of X-irradiation in combination with chemotherapy for the treatment of internal solid tumors may have a generalized therapeutic benefit, e.g., by destroying or inhibiting the proliferation of at least some tumor cells, such conventional treatment regimens are far from ideal. In particular, these adjunct therapies are limited by the potentially toxic side effects which stem from the lack of specificity of the chemotherapeutic agents.

SUMMARY OF THE INVENTION

The present invention overcomes the problems of conventional approaches for the treatment of solid tumor malignancies by combining with radiation therapy a method which specifically targets the tumor for destruction by the patient's cellular immune system. In essence, the method of the invention is a synergistic combination of two therapeutic methods, X-irradiation and photopheresis, each of which is known to be efficacious for treating a different disease state. Applicants' invention is the discovery that when combined, these two methods exert a synergistic therapeutic benefit in treating a subject having a solid tumor malignancy. Because modulation of the cellular immune response is important to the execution of the invention, it is preferred that the recipient subject of the cellular vaccine which mediates the cellular immune response (described below) have a competent immune system, as evidenced by, for example, near normal absolute levels of CD8 positive T cells.

According to one aspect of the invention, a method for improving the effectiveness of radiation therapy for treating a subject having an internal solid tumor is provided. The method involves irradiating the internal solid tumor to release tumor-derived antigens, isolating a plurality of these antigens and contacting the tumor-derived antigens with a leukocyte preparation that previously has been subjected to photopheresis, i.e., irradiated in the presence of a photoactivatable agent to form a photoinactivated leukocyte preparation. The tumor-derived antigens are contacted with the photoinactivated leukocyte preparation under conditions for forming the cellular vaccine, which vaccine is then administered to the subject to improve the effectiveness of the radiation therapy. Alternative methods can be employed to release, in vivo, antigens from the solid tumor. These include physical manipulation of the tumor (e.g., at the time of surgery), such as squeezing the tumor, perfusing or injecting the tumor with a high concentration of a saline solution or a chemotherapeutic agent(s). Additional methods for effecting the in vivo release of antigens from the tumor include arterial chemoperfusion (i.e., perfusing a tumor by injecting a high concentration(s) of a chemotherapeutic agent(s) into an artery leading into the tumor-containing organ); photofrin (i.e., administering to the tumor via systemic or perfusion routes, a photoactivatable agent such as a porphyrin, followed by photoactivating the agent in situ), and damaging the tumor with laser light of a sufficient wavelength and intensity to effect the release of antigens from the tumor in vivo.

In the preferred embodiments, the tumor-derived antigens are released from the tumor in viva following X-ray irradiation ("X-irradiation") of the tumor. Alternative methods for site-directed tumor necrosis, which methods are sufficient to release circulating tumor-derived antigens in viva, are contemplated as being within the scope of the instant invention.

According to another aspect of the invention, a cellular vaccine for improving the effectiveness of radiation therapy is provided. The cellular vaccine includes an effective amount of an admixture containing a plurality of solid tumor-derived antigens admixed with a plurality of antigen presenting cells that have been treated to induce expression of empty class I and/or empty class II major histocompatibility complex molecules. Typically, such induction is accomplished by photopheresis and the induced cells are referred to as "photoinactivated" antigen presenting cells. The admixture is placed in a pharmaceutically-acceptable carrier.

As used herein, an "effective amount" of the admixture is that amount sufficient for improving the effectiveness of radiation therapy for treating the subject. Whether the amount is an "effective amount" is determined according to criteria known to one of ordinary skill in the art. In the preferred embodiments, the antigen presenting cells used for preparing the cellular vaccine are autologous cells, i.e., isolated from the recipient subject, that have been photoinactivated by subjecting a leukocyte preparation to photopheresis. However, alternative sources of antigen presenting cells and methods for producing the functional equivalent of photoinactivated leukocytes also are provided. Because the solid tumor-derived antigens are isolated from body fluids such as whole blood, lymphatic fluid and possibly urine, the cellular vaccine optionally includes a detectable amount of the body fluid from which the antigen was isolated.

According to another aspect of the invention, a method for making the above-described cellular vaccine is provided. The method includes isolating a plurality of tumor-derived antigens, exposing a leukocyte preparation to irradiation in the presence of a photoactivatable agent to form a photoinactivated leukocyte preparation and contacting the plurality of tumor-derived antigens with the photoinactivated leukocyte preparation under conditions for forming the cellular vaccine. If the admixture is not already contained in a pharmaceutically acceptable carrier, it is placed in such a carrier prior to administration to the subject.

An alternative method for improving the effectiveness of radiation therapy for treating a subject having an internal solid tumor also is provided. The method includes irradiating the solid tumor to release tumor-derived antigens in vivo, isolating a plurality of the tumor-derived antigens, treating a cellular preparation (containing antigen presenting cells that are suitable for administration to the subject) to enhance surface expression by the cells of a major histocompatibility complex molecule, contacting the tumor-derived antigens with the treated cellular preparation under conditions for forming a plurality of antigen-associated antigen presenting cells, and administering the antigen-associated antigen presenting cells to the subject. Methods for treating the cellular preparation to enhance expression of the major histocompatibility molecules include, for example, subjecting the cellular preparation to one or more of the following extracorporeal procedures or conditions: (1)

photopheresis, (2) temperatures less than physiological temperatures and (3) contacting the cellular preparation with one or more cytokines known to induce expression of the major histocompatibility molecules. In a preferred embodiment, the antigen presenting cells are autologous cells, i.e., the cells are isolated from the recipient subject. More preferably, the cells are monocytes or B-cells.

According to another aspect of the invention, a method for enhancing an immune system response to a tumor specific antigen is disclosed. The method includes releasing a plurality of tumor-derived antigens in vivo, isolating the tumor-derived antigens and contacting the isolated antigens with a cellular preparation containing antigen presenting cells, which preparation has been treated to enhance expression by cells of empty major histocompatibility complex molecules. Preferably, the antigen presenting cells are leukocytes, more preferably monocytes or B-cells. In the preferred embodiments, the cellular preparation is treated to enhance expression of empty major histocompatibility complex molecules by any of the above-mentioned extracorporeal procedures, e.g., subjecting the cellular preparation to photopheresis and/or to a temperature less than a physiological temperature. The cellular vaccine for enhancing the immune system to a tumor specific antigen is formed by contacting the above-described cellular preparation with the plurality of tumor-derived antigens under conditions known to enhance association of the antigens with the empty major histocompatible molecules present on the surface of the antigen presenting cells. Thereafter, the vaccine is administered to the subject in accordance with methods known to one of ordinary skill in the art.

These and other aspects of the invention, as well as various advantages and utilities, will be more apparent with reference to the detailed description of the preferred embodiments and in the accompanying drawings.

DETAILED DESCRIPTION OF THE INVENTION

Figure 1:
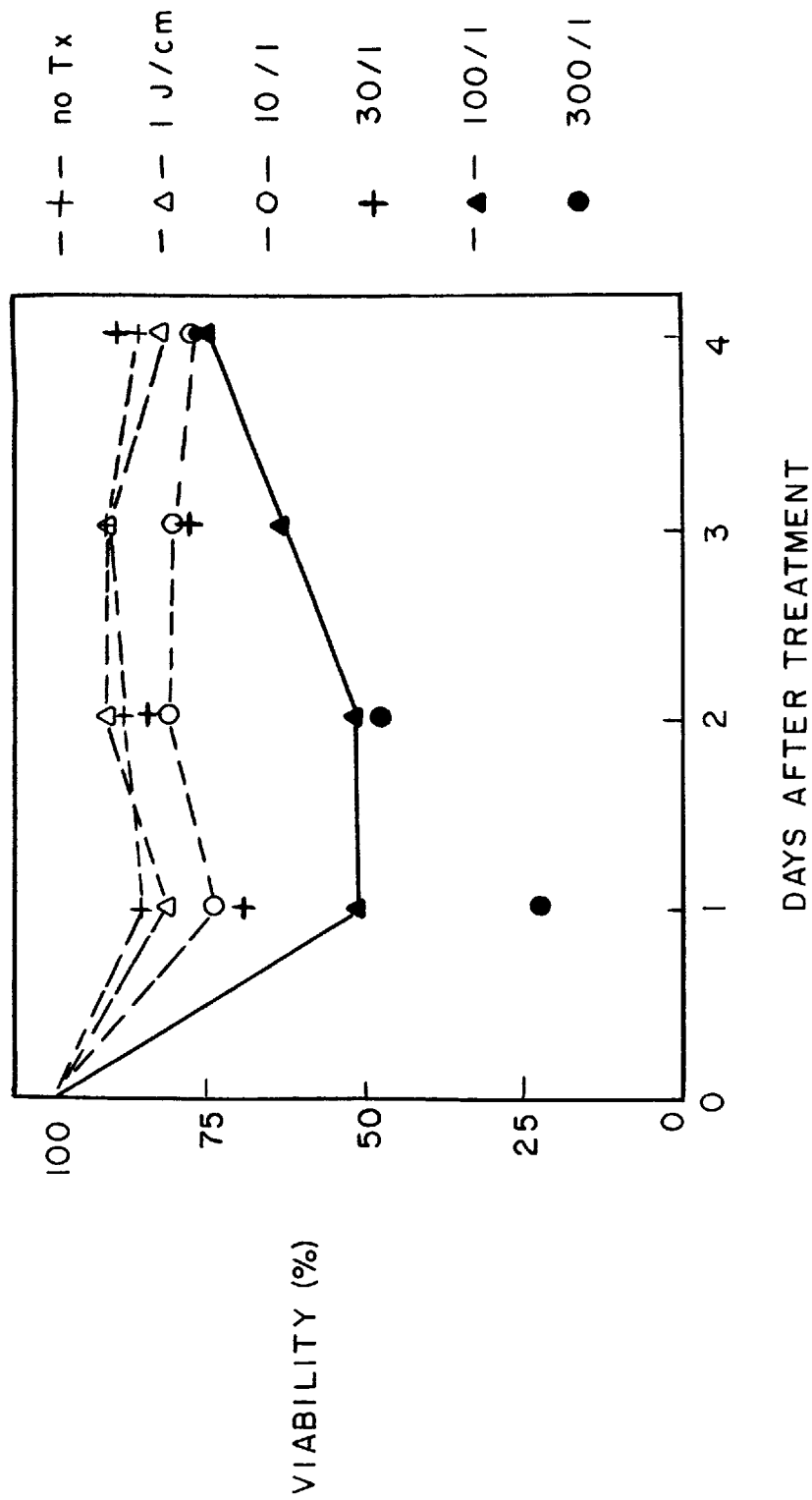
FIG. 1 shows the effects of 8-MOP and UVA on the survival of RMA cells, as determined by trypan blue exclusion.

A method for improving the effectiveness of radiation therapy for treating a subject having an internal solid tumor malignancy is provided. The method synergistically combines two therapeutic methods: X-irradiation for the treatment of an internal solid tumor malignancy and a method for stimulating the immune system to specifically recognize tumor-specific antigens. The tumor-specific antigens are released from the solid tumor following irradiation. The specific immune response is mediated by administration of a cellular vaccine (described below) containing the tumor-derived antigens. In its simplest form, the cellular vaccine includes an effective amount of an admixture containing a plurality of the tumor-derived antigens admixed with a plurality of photoinactivated leukocytes. The admixture is contained in a pharmaceutically acceptable carrier.

The preferred method for improving the effectiveness of radiation for treating a subject having an internal solid tumor involves irradiating the internal solid tumor to release the tumor-derived antigens in vivo, isolating a plurality of the tumor-derived antigens and contacting the isolated antigens with a photoinactivated leukocyte preparation to form the cellular vaccine. In the most preferred embodiments, the photoinactivated leukocyte preparation is formed by irradiating the leukocyte preparation with ultraviolet A radiation ("UVA") or visible light in the presence of a photoactivatable agent, i.e., by subjecting the leukocyte preparation to photopheresis. Conditions for activating psoralens in the presence of visible light are disclosed in U.S. application Ser. No. 08/013,831, filed Feb. 4, 1993, now issued as U.S. Pat. No. 5,462,733, the entire contents of which patent application are incorporated herein by reference. The cellular vaccine is formed by admixing the solid tumor-derived antigens with the photoinactivated leukocyte preparations under conditions for loading the tumor-derived antigens into the empty class I or class II major histocompatibility complex molecules of the antigen presenting cells. In general, such conditions include admixing the cells at temperatures between about 22° C. and about 30° C. to enhance the stability of the empty class I or class II molecules. Exemplary conditions for loading the antigens into empty class I major histocompatibility complex molecules are disclosed in Example 3.

As recited in the above-identified U.S. application Ser. No. 08/013,831, now issued as U.S. Pat. No. 5,462,733, methods other than photoinactivation with UVA light in the presence of a psoralen are useful for preparing a preparation of cells having enhanced expression of empty class I and/or empty class II major histocompatibility complex molecules. Exemplary alternative methods include ultraviolet B ("UVB") irradiation, contacting the cells with a chemotherapeutic agent(s) and/or a cytokine(s) such as tumor necrosis factor (TNF), exposing the cells to temperatures in the range of about 22° C. to about 30° C., exposing the cells to hypotonic or hypertonic saline solution or tissue culture medium and exposing the cells to hydrostatic pressure.

Empty class I molecules are thermodynamically unstable at physiological temperatures. Accordingly, it is believed that exposure of the cellular preparation to a temperature that is less than physiological temperatures results in "enhanced expression" of the empty major histocompatibility complex class I molecules by stabilizing the "empty" molecules. As used herein, the term "enhanced expression" refers to a cell having on its surface substantially more empty major histocompatibility complex molecules than would be present on the surface of a corresponding, naturally occurring antigen presenting cell.

The cellular vaccine is administered to the subject according to any appropriate mode of administration known in the art, e.g., introduction into the blood stream or the immune system of the patient. Intradermal injection is a preferred method of administration. However, subcutaneous injection, intramuscular injection and/or any other mode of depositing the cellular vaccine in a reservoir such that the tumor-derived antigens are exposed to the subject's cellular immune system, i.e., the cells comprising the cellular immune system can recognize and react to the presence of the tumor-derived antigen, can be used. Accordingly, the cellular vaccine further includes a pharmaceutically acceptable carrier that is appropriate for the selected mode of administration. Pharmaceutically acceptable carriers are known in the art and include, for example, normal saline for vaccines intended for administration by injection into the blood system.

In the preferred embodiments, the subject is a human having an internal solid tumor that is amenable to X-irradiation therapy. As used herein, the phrase "amenable to X-irradiation therapy" in reference to a solid tumor means a tumor which contains at least some tumor cells that are susceptible to cellular damage in response to irradiation, which damage is sufficient to release tumor-derived antigens in vivo.

The term "irradiation" as used herein, has its conventional meaning and is only limited to the extent that the X-irradiation have sufficient energy to penetrate the body and be capable of inducing the release of tumor-specific antigens in vivo. The optimal radiation intensity for damaging a particular type of tumor is known to one of ordinary skill in the art. In general, any form or intensity of radiation that is acceptable in the art for treating internal solid tumors is useful for releasing tumor-derived antigens in vivo for the purposes of the instant invention.

Radiation is measured in RADS, with a typical dosage of X-irradiation falling between about 1000 to about 4000 RADS for tumor irradiation therapy. The radiation dosage range for the instant invention falls within the range of about 100 to about 6000 RADS. Since less radiation is needed to damage the tumor to induce the release of tumor-derived antigens in vivo than is needed to destroy the tumor (the objective of conventional radiation therapy), the instant invention advantageously permits the use of lower dosages of radiation, thereby avoiding the toxic side effects associated with high doses of X-irradiation. Typically, the radiation is administered in fractioned doses over several weeks with no more than 300 RADS being administered per treatment.

Because the combination therapy of the instant invention enlists the subject's immune system to specifically target and destroy the internal tumor, it is preferred that the recipient subject of the combined therapy have a competent immune system. In general, the immunocompetence of a particular subject is determined by measuring the amount of CD8 positive T cells in a blood sample taken from the subject. Subjects having near normal absolute levels of CD8 positive T cells are deemed to be immunocompetent for the purposes of the instant invention. In general, a subject having a CD8 level that is at least about 100 CD8 cells/100 ml blood is deemed to be immunocompetent.

The phrase "internal solid tumor" refers to an extracutaneous, i.e., non-cutaneous T-cell lymphoma, neoplasm. Whether a particular treatment or combination therapy is efficacious in halting progression of the neoplasm is determined by criteria known to one of ordinary skill in the art. For example, efficacy can be demonstrated by observing a change in the rate of tumor growth (e.g., a static or reduced rate of growth as evidenced by the rate of change in the size of the tumor with time) and/or by observing a slowing in the progression of the disease state (e.g., a reduction in disease-associated symptoms with time). Such criteria are useful for determining whether the solid tumor is amenable to radiation therapy, as well as for assessing whether the methods and/or compositions of the instant invention improve the effectiveness of radiation therapy for treating the subject. Exemplary solid tumor malignancies amenable to treatment by the methods and compositions of the instant invention are listed above.

X-irradiation induced cell damage or death results in the in vivo release of a myriad of oligopeptides, proteins and/or other cellular components from the irradiated cells. These previously immobile (i.e., associated with the solid tumor) cellular components enter the lymphatic and/or blood systems from which they can be isolated according to procedures well known in the art. As used herein, the term "isolated" refers to a preparation (e.g., a collection of tumor-derived antigens or a leukocyte preparation) that has been removed from its naturally occurring environment. Thus, for example, a blood sample withdrawn from a subject is "isolated" as defined herein, even if the blood sample is part of a continuous stream that is later reinfused into the subject.

The term "tumor-derived antigens" refers collectively to components which are released from the solid tumor following irradiation. There is no requirement that the tumor-derived antigens be purified or concentrated prior to their use in accordance with the methods or compositions of the instant invention. However, the concentration of tumor-derived antigens in the isolated preparation optionally is enriched prior to storage to enhance the stability of the antigen upon storage. By "enriched" it is meant that the tumor-derived antigen is present at a higher concentration than that which it was present when isolated from the subject. In general, an enriched preparation of tumor-derived antigens is preferred because the higher concentration of antigen, when admixed with the treated antigen presenting cells, kinetically favors the loading of tumor-derived antigen into the empty class I or empty class II major histocompatibility complex molecules of the treated antigen presenting cells.

Antigen storage conditions are known to those of ordinary skill in the art and include, for example, storage at a reduced temperature (e.g., at −70° C.) in the presence of protein stabilizing agents such as protease inhibitors and/or agents known to stabilize the native conformation of peptide and/or protein antigens (e.g., dimethyl sulfoxide (DMSO)). Such agents are known to one of ordinary skill in the art and include, for example, glycerol, sucrose and urea.

The cellular vaccine is prepared by contacting the tumor-derived antigens with a cellular preparation that has been "altered" (e.g., photoinactivated) to enhance interaction (e.g., association) of the tumor-derived antigens with the cells contained in the cellular preparation. As used herein, the phrase "cellular preparation" refers to a preparation of antigen presenting cells. Antigen presenting cells are a class of cells capable of presenting antigen to other cells of the immune system that are capable of recognizing antigen when it is associated with a major histocompatibility complex molecule. Antigen presenting cells include such diverse cell types as leukocytes (e.g., monocytes, macrophages and lymphocytes such as T cells and B cells), as well as synthetic ("artificial") cells such as those described in U.S. patent application Ser. No. 07/977,672, now issued as U.S. Pat. No. 5,651,993, the contents of which patent application are incorporated herein by reference. These diverse cell types have in common the ability to present antigen in a form that is recognized by specific T cell receptors. The preferred antigen presenting cells are leukocytes, more preferably, monocytes or B-cells. The leukocyte preparation is isolated from, for example, blood, lymph fluid, bone marrow, lymphatic organ tissue or tissue culture fluid. Optionally, the monocytes or B-cells are cultured in vitro to expand the number of cells available for forming the cellular vaccine in vitro.

As previously discussed, each T lymphocyte clone, e.g., T-helper cell clone or cytotoxic T cell clone, expresses a different surface receptor which recognizes an antigen only when it is associated with a major histocompatibility complex molecule on the surface of the antigen presenting cell. In general, the term "major histocompatibility complex molecule" refers to a molecule on an antigen presenting cell that has the ability to associate with the antigen to form an antigen-associated antigen presenting cell. Recognition of the antigen-associated presenting cell by the T cell is mediated by the T cell surface receptor. In the preferred embodiments, the major histocompatibility complex molecule is a class I or class II molecule. A cytotoxic T cell binds antigen when the antigen is associated with a major histocompatibility complex class I molecule. A T helper cell recognizes and binds antigen when the antigen is associated with a major histocompatibility complex class II molecule. Each of these T cell types functions to mediate the subject's immune response to the tumor.

The class I molecule, composed of a heavy chain and a noncovalently linked beta-2-microglobulin molecule, includes a cleft or crevice for receiving the tumor-derived antigen. Accordingly, the preferred tumor-derived antigen has a size and dimension that permit entry of the antigen into the crevice of the class I molecule. (See e.g., F. Latron, "A Critical Role for Conserved Residues in the Cleft of HLA-A2 in the Presentation of a Nonapeptide to T-cells", *Science* 257:964–967 (1992) for a discussion of class I molecule cleft dimensions). Although the tumor-derived antigen fits substantially within the crevice, it is still accessible to a T cell capable of recognizing the antigen when it is associated with the class I molecule. Thus, in a preferred embodiment, the tumor-derived antigen is a peptide having between about eight and about sixteen amino acids. In a most preferred embodiment, the tumor-derived antigen is a peptide having between eight and ten amino acids, two of which amino acids are hydrophobic residues for retaining the peptide in the crevice. Association of the tumor-derived antigen with the class I molecule is determined using screening assays that are capable of distinguishing between empty and full class I molecules. An exemplary screening assay is disclosed in Example 3.

Association of a tumor-derived antigen with a major histocompatibility molecule of an antigen presenting cell is a prerequisite for inducing the cellular immune response to the tumor. Accordingly, various methods are disclosed herein for enhancing expression of empty major histocompatibility molecules on the surface of the antigen presenting cells.

The preferred method for enhancing expression of empty major histocompatibility molecules is photopheresis. Photopheresis procedures are described in U.S. Pat. No. 5,147,289 ("Edelson '289") and U.S. Pat. No. 4,838,852 (Edelson '852), the entire contents of which patents are incorporated herein by reference. Photopheresis may be performed on a continuous stream, as described in the Edelson '289 patent, or may be performed batchwise. It is believed that subjecting the preparation to photopheresis disrupts the cells' metabolic pathways responsible for processing intracellular antigen into a form that fits within the crevice defined by the major histocompatibility complex molecule, thereby yielding a plurality of antigen presenting cells having unfilled (i.e., "empty") major histocompatibility complex molecules on their surface. These photoinactivated cells bind tumor-derived antigens having the above-described requisite size and charge characteristics. Once bound, the tumor-derived antigen-associated antigen presenting cells are administered to the subject in the form of a cellular vaccine.

If the photoactivatable agent is a psoralen (described below), the radiation for photoactivation is ultraviolet A irradiation or visible light having a wavelength greater than about 420 nm (Gasparro, F., et al., "The Excitation of 8-methoxypsoralens with Visible Light. Reversed Phase HPLC Quantitation of Monoadducts and Crosslinks", *Photochemistry and Photobiology* 57:1007–1010 (1993)).

Yet another method for enhancing expression of empty major histocompatibility complex molecules, is to contact the cellular preparation with a cytokine. The term cytokine denotes the molecules previously referred to in the literature as lymphokines, monokines, interleukins, interferons and tumor necrosis factor (TNF) (*Essential Immunology*, 7th edition, Blackwell Scientific Publications, Oxford, Great Britain, pp. 140–150 (1991)) and includes, for example, gamma-interferon, tumor necrosis factor alpha and granulocyte monocyte colony stimulating factor, as well as molecules in the family of interleukins. Cytokines are known to increase expression of the major histocompatibility complex molecules on some antigen presenting cells, e.g., monocytes or B-cells.

The above-described altered antigen presenting cells, e.g., altered by photopheresis or exposure to a cytokine, are contacted with the tumor-derived antigens under conditions for forming the cellular vaccine. As used herein, the phrase "cellular vaccine" refers to a preparation of cells which, when introduced into a subject, elicits a cellular immune response that is specific for a component (e.g., the tumor-derived antigen) present in the cellular vaccine. The term "vaccine" is used herein because although only a small portion of the subject's total leukocytes are treated, a far-reaching therapeutic effect is obtained with respect to the irradiated tumor following infusion of the vaccine.

In the preferred embodiments, the cellular vaccine is stored prior to administration to the subject. Preferably, the vaccine is stored in aliquots containing an amount of tumor-derived antigen-associated antigen presenting cells sufficient to boost the cellular immune response of the subject to the solid tumor. Determination of the amount of vaccine necessary to boost the patient's immune response is within the ordinary skill of the art. Preferably, an amount of cells ranging from a minimum of about 10,000 to a maximum of about $200\times10^6$ antigen presenting cells is sufficient to boost the immune response of the subject. The amount of cells used will, in part, be dependent upon whether the antigen presenting cells are efficient, e.g., B cells or monocytes, or inefficient, e.g., T cells.

The antigen and cellular components of the cellular vaccine differ from their corresponding natural counterparts in several respects. The antigen-associated antigen presenting cells of the instant invention represent a relatively homogeneous population of cells. This is primarily because the tumor-derived antigen is not further processed by the antigen presenting cells prior to association with the major histocompatibility complex molecule on the surface of the antigen presenting cell. Second, the antigen presenting cells of the present invention optionally have an elevated concentration of major histocompatibility complex molecules on a per cell basis. Moreover, the pharmaceutical composition optionally includes beta-2 microglobulin to facilitate association of the antigen with the major histocompatibility complex molecules. The concentration of beta-2 microglobulin in the preparation is greater than that which would be found in vivo. Selection of the concentration of beta-2 microglobulin necessary to augment association of the tumor-derived antigen with the major histocompatibility complex molecule is within the ordinary skill in the art. In general, the in vivo concentration of beta-2 microglobulin is in the range of about 0.2 to about 100 ug/ml, more preferably between about 2.0 to about 10 ug/ml (Rock et al., Proc. Natl. Acad. Sci. (USA) 87:7517–7521 (1990).

The cellular vaccine stimulates the immune system to specifically recognize the tumor of the recipient subject, thereby improving the effectiveness of radiation therapy for treating the subject. Although the cellular preparation typically is a leukocyte-containing preparation, other types of antigen presenting cells are deemed to be within the scope of the instant invention. Accordingly, the term "functional equivalent" of a photoinactivated leukocyte preparation refers to an antigen presenting cell-containing preparation that has been treated by photochemical (e.g., photopheresis) or non-photochemical (e.g., exposure of the cell to reduced temperatures) methods to enhance expression of the empty major histocompatibility complex molecules on the surface of the cells present in the preparation.

The irradiation step takes place in the presence of a photoactivatable agent. Other methods (described above) for inducing expression of the empty major histocompatibility-complex molecules can be used. The photoactivatable agent may be any agent which has an affinity for an important component of the leukocyte or other antigen presenting cell and which, upon binding to the component, enhances and/or stabilizes expression of the major histocompatibility complex molecules. Exemplary photoactivatable agents are psoralens, porphyrins, pyrenes, phthalocyanine, photoactivated cortisone, photoactivated antibodies specifically reactive with the antigen presenting cell, and monoclonal antibodies which have been linked to porphyrin molecules.

The psoralens are a preferred class of photoactivatable agents. The interactions of psoralens with the DNA, protein and lipid components of T cells have been described ("T Cell Molecular Targets for Psoralens", *Annals of N.Y. Academy of Science* 636:196–208 (1991), Malane, M. and Gasparro, F. Following oral administration, psoralens are absorbed from the digestive tract, reaching peak levels in the blood and other tissues in one to four hours and are excreted almost entirely within 24 hours following oral administration. These agents can also be added directly to the extracorporeal cell preparation. The psoralen molecules are inert prior to exposure to ultraviolet or visible light irradiation and are transiently activated into an excited state following irradiation. These transiently activated molecules are capable of photomodifying biological molecules (e.g., DNA, protein) and generating other reactive species, e.g., singlet oxygen, which are capable of modifying other cellular components. Other agents, e.g., mitomycin C and cis-platinum compounds, damage DNA by crosslinking strands of the nucleic acid. However, such agents remain in an active state when returned to the patient and thus are not as desirable as the psoralens for altering cells to enhance expression of empty major histocompatibility complex molecules.

Preferred psoralens include 8-methoxypsoralen (8-MOP), 4'-aminomethyl-4,5',8-trimethyl-psoralen (AMT), 5-methoxypsoralen (5-MOP) and trimethylpsoralen (TMP). 8-MOP is both an anti-cancer drug, an immune system modulator and a prototype for the development of a class of drugs that are photoactivatable. AMT is a synthetic, water soluble analogue of 8-MOP. This and other synthetic water soluble analogues of 8-MOP are described in Berger et al., "The Medical and Biological Effects of Light", *Annals of N.Y. Academy of Science* 453:80–90 (1985). Some investigators have reported that 5-MOP is not as efficacious as 8-MOP in the treatment of psoriasis (Calzavara-Pinton, et al., *Exptl. Dermatol.* 1:46–51 (1992)). TMP is widely used to treat vitiligo patients resulting in the repigmentation of depigmented areas of skin.

Monoclonal antibodies which recognize 8-MOP-DNA photoadducts in irradiated cells may be used to determine the optimum amount of ultraviolet or visible light irradiation to achieve optimal cell photoinactivation (see Yang et al., "8-MOP DNA Photoadducts in Patients Treated with 8-MOP and UVA", *J. Invest. Dermatol.* 92:59–63 (1989).

Each of the references, patents and patent applications recited in this specification are incorporated herein by reference. It should be understood that the preceding is merely a detailed description of certain preferred embodiments. It therefore should be apparent to those skilled in the art that various modifications and equivalents can be made without departing from the spirit or scope of the invention.

EXAMPLES

Example 1

Case Studies of Three Patients Diagnosed with Cutaneous T Cell Lymphoma (CTCL)

Tumor stage Cutaneous T Cell Lymphoma (CTCL) is well known to be unresponsive, in terms of survival of patients and prolonged disease-free periods, to conventional chemotherapy and Total Body Electron Beam (TBEB) radiotherapy. In general, the median survival time of a CTCL patient with two or more tumors greater than 3 cm in diameter is eighteen months.

Three case studies are presented below. In each study, a CTCL patient was treated with Total Body Electron Beam (TBEB) radiation and photopheresis therapy. Following treatment, each patient was examined monthly for skin tumors and received periodic skin biopsies and regular CAT Scans to determine if internal lymphomas had developed. In contrast to the expected progression of the disease, each of the CTCL patients described below has remained skin tumor-free.

(a) Patient M. K.

Patient Profile and Diagnosis: Patient M. K., a 68 year old white male dairy farmer, presented to us in February 1990 with wide spread skin tumors that had developed over a period of approximately one year. Skin biopies were performed and were diagnostic of CTCL; A CAT scan ruled out the presence of obvious internal lymphomas.

Therapy: M. K. received a total of 3600 RADS of Total Body Electron Beam (TBEB) radiation in two groups of 18 treatments (i.e., 100 RADS/treatment) over a nine week period. Approximately mid-way through TBEB radiation therapy, M. K. received photopheresis therapy (on two successive days) for the first time. M. K. continues to receive monthly photopheresis therapy on two successive days.

Patient Evaluation: Since treatment, M. K. has remained skin tumor-free.

(b) Patient C. Q.

Patient Profile and Diagnosis: Patient C. Q., a 64 year old white male executive, presented to us in 1986 with wide-spread, large skin tumors (i.e., tumors having a diameter greater than 3 cm). Skin biopies were performed and were diagnostic of CTCL; A CAT scan ruled out the presence of obvious internal lymphomas.

Therapy: C. Q. received a total of 3600 RADS of Total Body Electron Beam (TBEB) radiation in 36 treatments (i.e., 100 RADS/treatment; four treatments per week) over a nine week period. Approximately midway through TBEB radiation therapy, C. Q. received his first photopheresis therapy on two successive days. C. Q. continued to receive monthly photopheresis therapy on two successive days until 1992 when photopheresis therapy was discontinued.

Patient Evaluation: Since treatment (seven years), C. Q. has remained skin tumor-free.

(c) Patient C. D.

Patient Profile and Diagnosis: Patient C. D., a 48 year old white male executive, presented to us in 1988 with more than fifty skin tumors, including a very large (i.e., a tumor having a diameter greater than 7 cm) ulcerated tumor on his right thigh. Skin biopies were performed and were diagnostic of CTCL; A CAT scan ruled out the presence of obvious internal lymphomas.

Therapy: C. D. received a total of 3600 RADS of Total Body Electron Beam (TBEB) radiation in 36 treatments (i.e., 100 RADS/treatment; four treatments/week) over a nine week period. Approximately midway through the TBEB radiation therapy, C. D. received his first photopheresis therapy on two successive days. C. D. continues to receive monthly photopheresis therapy on two successive days.

Patient Evaluation: Since treatment, C. D. has remained skin tumor-free.

Example 2

Case Study of a Patient Diagnosed With Metastatic Colon Carcinoma

Patient Profile and Diagnosis: Patient S. C., a 78 year old white male presented to us with a severe productive cough (coughing up bright red blood) and was diagnosed as having metastatic colon carcinoma and lesions in the lung and liver. Biopsy of the lung lesion by bronchoscopy demonstrated that the large mass in the patient's right lung was colon carcinoma.

Therapy: S. C. initially was treated with 5-fluorouracil chemotherapy but failed to respond. Subsequently, S. C. received a total of 3000 RADS of X-irradiation to the lung lesion in ten divided doses of 300 RADS each over a 12 day period. The liver lesion did not receive X-irradiation. Approximately midway through the X-irradiation therapy, S. C. received his first photopheresis therapy on two successive days. Monthly photopheresis therapy on two consecutive days was continued for four months.

Patient Evaluation: At the end of the fourth month of photopheresis therapy, the liver metastases was still present (as determined by CAT scan), but the lung lesion was no longer evident. As assessed by periodic CAT scans, the lung remained tumor-free until the patient's death approximately three years following the initial X-irradiation/photopheresis treatment.

Example 3

8-MOP/UVA Induction of Empty MHC Class I Molecules at the Cell Surface: Association of Empty MHC Class I Molecules with Exogenous Peptide.

EXPERIMENTAL DESIGN:

Overview: RMA cells (Ljunggren et al., Nature 346:476–480 (1990)) were assayed by cytofluometry for empty class I expression following treatment with 8-MOP/UVA to determine whether 8-MOP/UVA uncouples the transport of peptide associated-MHC class I complexes to the cell surface. The phototreated cells were exposed to temperatures that specifically enhance the appearance of empty class I MHC (about 28° C.). Following photoinactivation, the empty class I molecules were quantitated by adding either of two peptides (Sequence I.D. Nos. 1 and 2), each of which was known to bind and stabilize MHC molecules (two specific influenza nucleoprotein fragments). To determine whether the treated cells released oligopeptides that bind to class 1, the empty class I molecules also were quantitated initially following treatment.

Cells. Murine RMA cells that contain only a few empty class I molecules and RMA-S cells, a mutant cell line, in which empty class I molecules have been shown to be stable at room temperature but labile at body temperature were provided by P. Cresswell (Yale Immunobiology).

8-MOP/UVA Treatment. RMA cells suspended in PBS were exposed to therapeutic doses of 8-MOP (20–200 ng/ml) and UVA (1–10 J/cm$^2$) in order to determine the specific sensitivity of these cells to phototreatment. Viability was assayed by trypan blue exclusion immediately after treatment.

Immunochemicals. Monoclonal antibodies with specific reactivities toward class I MHC ($K^b$, Y3 murine hybridoma ATCC No. HB176 and $D^b$, 28148S murine hybridoma ATCC No. HB27) were obtained from ATCC (Rockville Md.). Influenza virus nucleoprotein oligopeptides (NP365–380 and NP345–360) were prepared at the Keck Protein Center. The $K^b$ binding 16 mer (Sequence I.D. No. 2 having the sequence SFIRGTKVSPRGKLST) and the $D^b$ optimally binding 9 mer (Sequence I.D. No. 1 having the sequence AENENMETM) were dissolved in IMDM (Iscove's modified Dulbecco's medium, GIBCO, Grand Island N.Y.) media in PBS at 50 uM and stored at 4° C.

FACS Analysis of MHC class I molecules. RMA-S cells served as positive controls for the expression of class I MHC molecules. The cells were cultured in 5% IMDM, 10% fetal calf serum (FCS) supplemented with 1% pen-strep antibiotics (GIBCO). Cells were removed from incubation (37° C., 5% $CO_2$), cultured in tissue flasks ($10^6$/ml) with tightened caps. To determine the thermal lability/stability of class I molecules, the cells were incubated in an adjustable water bath for 48 hrs at a given temperature. For cytofluorometric assays, $2\times10^6$ cells were incubated on ice with 10% human serum type AB (GIBCO), then with 0.15 ml anti-class I monoclonal antibody tissue culture supernatant for 30 min on ice, washed twice with PBS, and then incubated with 0.15 ml fluorescein isothiocyanate (FITC)-conjugated goat anti-mouse immunoglobulin (Sigma, St Louis Mo.) on ice for 30 min, washed twice with PBS, fixed in 1% formaldehyde and analyzed on a FACS cell sorter. To stabilize class I MHC molecules, influenza nucleoproteins fragments (Sequence I.D. Nos. 1 or 2) were added (50 uM).

RESULTS:

FIG. 1 shows the effects of 8-MOP (10–300 ng/ml) and UVA (1 J/cm$^2$) on the survival of RMA cells (as determined by trypan blue exclusion). The viability of cells which were not exposed to 8-MOP or UVA are designated "no Tx" (i.e., no treatment) in the figure. The viability of cells which were exposed to UVA but which were not exposed to 8-MOP are designated "1 J/cm" in the figure. A dose-dependent increase in cell damage was observed with increasing doses of 8-MOP used in combination with 1 J/cm$^2$. The increasing doses are indicated in the figure (i.e., the designations of 10, 30, 100 and 300 refer to the concentration of 8-MOP in ng/ml).

Figure 2:
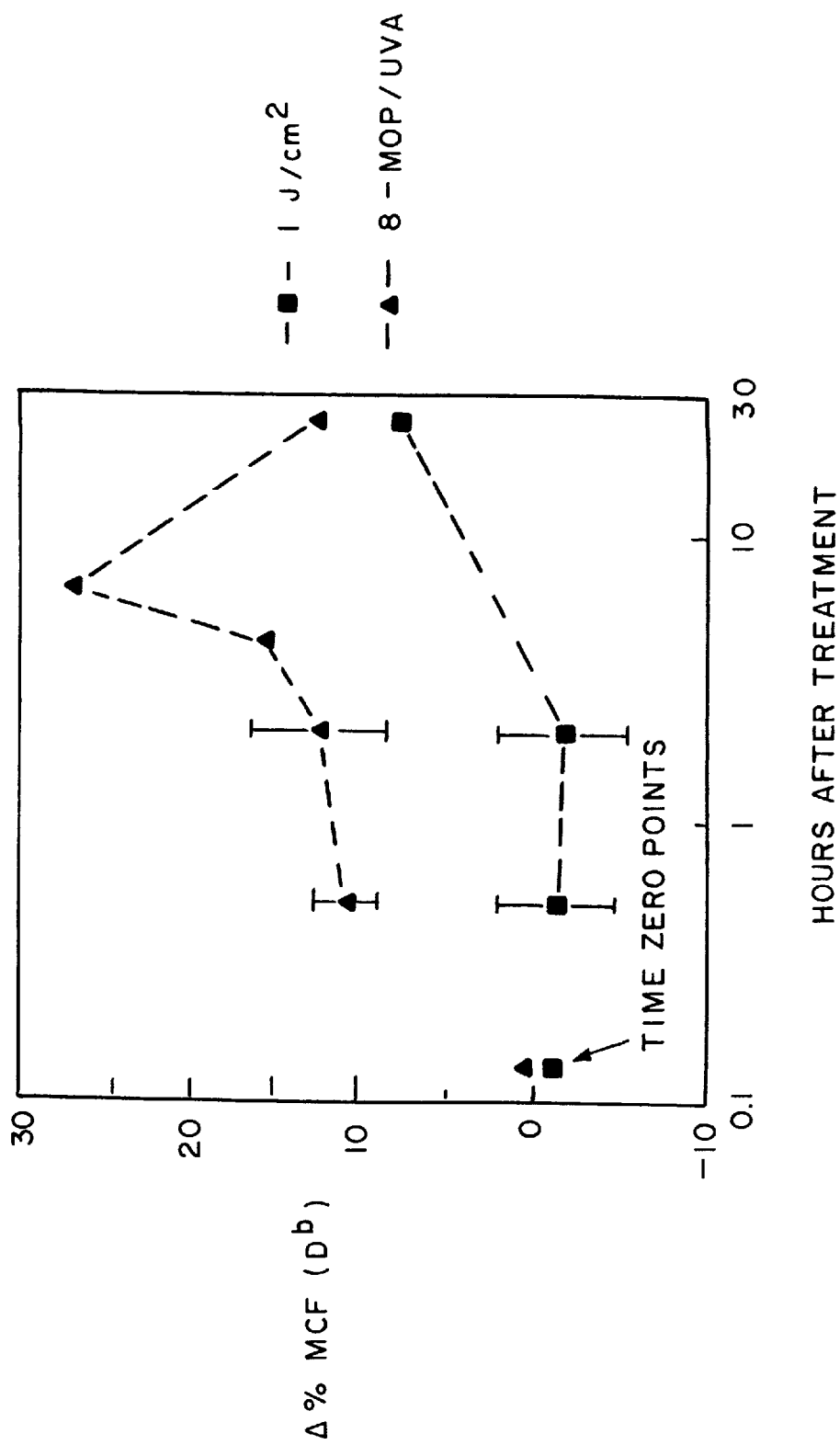
FIG. 2 shows the time course for enhancement of $D^b$ class I MHC molecules on RMA cells treated with 100 ng/ml 8-MOP and 1 J/cm$^2$ UVA for a composite set of experiments.

The effects of 8-MOP (100 ng/ml) and UVA (1 J/cm$^2$) on class I expression and the binding of specific oligopeptides (Sequence I.D. No. 1) to RMA class I molecules was determined. FIG. 2 represents a composite set of experiments showing the time course for enhancement of $D^b$ class I MHC molecules on RMA cells treated with 100 ng/ml 8-MOP and 1 J/cm$^2$ UVA. In this series of experiments, the 8-MOP/UVA treated cells were compared to cells exposed to UVA alone (1 J/cm$^2$).

FACS analysis was used to gauge the extent of class I expression using ATCC antibodies specific for $D^b$ class I molecules. The change in mean channel fluorescence (Δ% MCF) was calculated by taking the difference in signal for cells incubated with and without the class I oligopeptide (Sequence I.D. No. 2, i.e., AENENMETM). FIG. 2 illustrates that the optimal signal (i.e., greatest increase in class I molecule expression) was detected within 10 hrs of 8-MOP/UVA treatment. An additional set of untreated control cells (designated "No Tx" in the figure) also was assayed. The optimal time for inducement of class I expression is determined by performing more detailed kinetic studies, e.g., by assaying the cells at more frequent intervals and at several different temperature conditions following 8-MOP/UVA treatment.

Antigens are selected for their ability to associate with empty class I molecules using the above-described FACS method. Thus, the FACS assay serves as a screening protocol for selecting the optimum conditions for inducing empty class I molecule expression, as well as a screening protocol for selecting antigens that are capable of binding to and stabilizing the empty class I molecules. In this manner, various peptides, and the optimum concentrations for each, are screened for their ability to stabilize empty class molecules.

Each of the above-recited patents and references is incorporated herein by reference. It should be understood that the preceding is merely a detailed description of certain preferred embodiments. It therefore should be apparent to those skilled in the art that various modifications and equivalents can be made without departing from the spirit or scope of the invention.

We claim:

1. A method for improving the effectiveness of X-irradiation therapy for treating a subject having an internal solid tumor, the method comprising:

(a) irradiating the internal solid tumor with X-irradiation having sufficient energy to induce release by the tumor of tumor-derived antigens;

(b) isolating a mixture of said tumor-derived antigens from the subject;

(c) exposing a leukocyte preparation containing a mixture of leukocytes to ultraviolet A or visible light irradiation in the presence of a photoactivatable agent to form a photoinactivated leukocyte preparation, said leukocytes expressing a mixture of major histocompatibility complex molecules;

(d) contacting said mixture of tumor-derived antigens with said photoinactivated leukocyte preparation under conditions for associating the tumor-derived antigens with the major histocompatibility complex molecules, thereby forming a mixture of antigen-associated leukocytes; and (e) administering said mixture of antigen-associated leukocytes to said subject.

2. The method of claim 1, wherein the internal solid tumors is associated with a cancer selected from the group consisting of the lung, breast, ovaries, uterus, prostrate, testicles, liver, pancreas, stomach, squamous cell carcinoma of the oral phalynx, fibrosarcomas, kidney, bladder, brain, spinal cord, malignant melanoma and metastatic squamous cell carcinoma of the skin.

3. The method of claim 1, wherein the mixture of antigen-associated leukocytes are administered to a subject having a competent immune system.

4. The method of claim 3, wherein the mixture of antigen-associated leukocytes are administered to a subject having a normal level of CD8 positive T cells.

5. The method of claim 1, wherein irradiating the internal solid tumor comprises irradiating the tumor with a total dosage of between 100 and about 6000 RADS.

6. The method of claim 1, wherein isolating the mixture of tumor-derived antigens comprises isolating said antigens from whole blood.

7. The method of claim 1, further comprising the step of preparing an antigen preparation having an enriched concentration of tumor-derived antigens.

8. The method of claim 1, further comprising the step of storing the mixture of tumor-derived antigens prior to contacting with said photoinactivated leukocyte preparation.

9. The method of claim 1, wherein said leukocyte preparation is isolated from the subject.

10. The method of claim 9, wherein said leukocyte preparation comprises a mixture of lymphocytes.

11. The method of claim 9, wherein said leukocyte preparation comprises a mixture of monocytes or B-cells.

12. The method of claim 11, further comprising the step of culturing said monocytes or said B-cells prior to exposing said preparation to irradiation.

13. The method of claim 10, wherein said leukocyte preparation is isolated from a source selected from the group consisting of blood, lymph fluid, bone marrow, lymphatic organ tissue and tissue culture fluid.

14. The method of claim 1, wherein exposing said leukocyte preparation to irradiation comprises exposing said leukocyte preparation to irradiation in the presence of a psoralen.

15. The method of claim 14, wherein said psoralen is selected from the group consisting of 8-methoxy psoralen, amino-methyl-trimethyl psoralen, 5-methoxy psoralen and trimethyl psoralen.

16. The method of claim 15, wherein said psoralen is 8-methoxy psoralen.

17. The method of claim 14, wherein said leukocyte preparation is exposed to visible light having a wavelength greater than about 420 nm.

18. The method of claim 1, wherein contacting said mixture of tumor-derived antigens with said photoinactivated leukocyte preparation is performed at a temperature between about 22° C. and about 30° C.

19. The method of claim 1, further comprising the step of storing the mixture of antigen-associated leukocytes prior to administering said mixture of antigen-associated leukocytes to the subject.

20. The method of claim 1, wherein administering said mixture of antigen-associated leukocytes comprises injecting said mixture of antigen-associated leukocytes into the bloodstream of the subject.

21. The method of claim 1, wherein administering said mixture of antigen-associated leukocytes comprises intradermal injecting said mixture of antigen-associated leukocytes.

22. A method for making a cellular vaccine for administration to a subject having an internal solid tumor, the method comprising:

(a) irradiating the internal solid tumor with X-irradiation having sufficient energy to induce release by the tumor of tumor-derived antigens;

(b) isolating a mixture of said tumor-derived antigens from the solid tumor;

(c) exposing a leukocyte preparation containing a mixture of leukocytes to ultraviolet A or visible light irradiation in the presence of a photoactivatable agent to form a photoinactivated leukocyte preparation, said leukocytes expressing a mixture of major histocompatibility complex molecules;

(d) contacting said mixture of tumor-derived antigens with said photoinactivated leukocyte preparation under conditions for associating the tumor-derived antigens with the major histocompatibility complex molecules, thereby forming a plurality of antigen-associated leukocytes; and (e) placing the mixture of antigen-associated leukocytes in a pharmaceutically acceptable carrier.

23. A method for improving the effectiveness of X-irradiation therapy for treating a subject having an internal solid tumor, the method comprising:

(a) irradiating the solid tumor with X-irradiation having sufficient energy to induce release by the tumor of tumor-derived antigens;

(b) isolating a mixture of said tumor-derived antigens from the subject;

(c) treating a cellular preparation containing a mixture of antigen presenting cells to enhance expression by said cells of a major histocompatibility complex molecule, each of said antigen presenting cells being suitable for administration to the subject;

(d) contacting said mixture of tumor-derived antigens with said treated cellular preparation under conditions for forming a mixture of antigen-associated antigen presenting cells; and (e) administering said mixture of antigen-associated antigen presenting cells to the subject.

24. The method of claim 23, wherein treating said cellular preparation comprises subjecting said preparation to a temperature between about 22° C. and 30° C.

25. The method of claim 23, wherein treating said cellular preparation comprises irradiating said cellular preparation in the presence of a photoactivatable agent.

26. The method of claim 23, wherein treating said cellular preparation comprises contacting said cellular preparation with one or more cytokines known to induce expression of a major histocompatibility molecule.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Ala Glu Asn Glu Asn Met Glu Thr Met
    1                   5

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Ser Phe Ile Arg Gly Thr Lys Val Ser Pro Arg Gly Lys Leu Ser Thr
    1             5                     10                   15